(12) United States Patent
Tsaur et al.

(10) Patent No.: US 10,695,456 B2
(45) Date of Patent: Jun. 30, 2020

(54) SKIN-FRIENDLY ABSORBENT STRUCTURE FOR PROVIDING OXYGEN

(71) Applicants: Garry Tsaur, Rowland Heights, CA (US); Ting-Hua Wang, Taichung (TW)

(72) Inventors: Garry Tsaur, Rowland Heights, CA (US); Ting-Hua Wang, Taichung (TW)

(*) Notice: Subject to any disclaimer, the term of this patent is extended or adjusted under 35 U.S.C. 154(b) by 456 days.

(21) Appl. No.: 15/592,107

(22) Filed: May 10, 2017

(65) Prior Publication Data
US 2017/0368223 A1 Dec. 28, 2017

(30) Foreign Application Priority Data

Jun. 27, 2016 (TW) .............................. 105209596 U

(51) Int. Cl.
| | |
|---|---|
| *A61L 15/18* | (2006.01) |
| *A61F 13/84* | (2006.01) |
| *A61F 13/02* | (2006.01) |
| *A61F 13/534* | (2006.01) |
| *A61L 15/20* | (2006.01) |
| *A61L 15/38* | (2006.01) |
| *A61L 15/42* | (2006.01) |
| *A61F 13/00* | (2006.01) |

(52) U.S. Cl.
CPC .......... *A61L 15/18* (2013.01); *A61F 13/0206* (2013.01); *A61F 13/534* (2013.01); *A61F 13/8405* (2013.01); *A61L 15/20* (2013.01); *A61L 15/38* (2013.01); *A61L 15/42* (2013.01); *A61F 13/00063* (2013.01); *A61F 2013/00604* (2013.01)

(58) Field of Classification Search
CPC ................ A61F 13/00063; A61F 13/15; A61F 13/8405; A61F 2013/8411; A61F 2013/8414; A61F 2013/8426; A61F 2013/8438; A61L 15/16; A61L 15/18; A61L 15/20; A61L 15/38; A61K 8/22; A61K 33/40; A61K 47/08
USPC ................................... 602/42.43, 48, 50, 53
See application file for complete search history.

(56) References Cited

U.S. PATENT DOCUMENTS

| | | | | |
|---|---|---|---|---|
| 4,959,216 A | * | 9/1990 | Daunter | ..................... A61F 6/08 128/832 |
| 5,778,886 A | * | 7/1998 | Shihata | ..................... A61F 6/06 128/830 |
| 2007/0156167 A1 | * | 7/2007 | Connors | ..................... A61F 2/06 606/194 |
| 2016/0114145 A1 | * | 4/2016 | Cook | ................ A61M 37/0069 435/395 |

* cited by examiner

*Primary Examiner* — Keri J Nelson
(74) *Attorney, Agent, or Firm* — Pai Patent & Trademark Law Firm; Chao-Chang David Pai

(57) ABSTRACT

A skin-friendly absorbent structure providing oxygen, comprising a absorbing layer and skin-friendly and oxygen-providing units, the skin-friendly and oxygen-providing unit being evenly dispersed in partial or entire scope of the absorbing layer wherein the skin-friendly and oxygen-providing unit comprises oxygen providing units and pH regulating units; and the pH of the skin-friendly absorbent structure is between 4 and 7 after absorbing liquids.

9 Claims, 5 Drawing Sheets

SKIN-FRIENDLY ABSORBENT STRUCTURE FOR PROVIDING OXYGEN

BACKGROUND OF THE INVENTION

1. Field of the Invention

The present invention relates to a skin-friendly absorbent structure for providing oxygen which may be disposed in personal hygiene products and release oxygen after absorbing liquids with the pH remaining skin-friendly neutral, weak acidic and slightly alkaline, thereby having no irritating effect on the skin.

2. Description of the Prior Art

There are various personal hygiene products contacting the body surface, such as sanitary napkins, diapers, cloth diapers, pasties, insoles, disposable underwear and oxygen providing paster units on the market. Most of these hygiene products emphasize the structural features of each layer as well as the comfort and convenience to wear thereof, but what is the most important is how to maintain human health when wearing them. Women will use sanitary napkins and tampons during the menstrual cycle, both of infants and children need to use diapers or cloth diapers before they can control to go to the bathroom, and the old and the people with difficulty in moving also choose and use adult diapers. The major components of sanitary napkins, tampons, diapers, cloth diapers or adult diapers are water absorbing materials, cotton, non-woven fabrics or polymeric fibers and they will entirely or partially cover the lower part of the body when in use.

When wearing sanitary napkins, diapers and cloth diapers, the wearer usually feels comfortable at the beginning except for poor material softness, contained inferior raw materials or fluorescent materials resulting in allergy. However, after wearing for a period of time and with the entry of blood, urine and sweat, the wearer will have an uncomfortable feeling, such as of stuffiness and wetness because the leak proof design and the closeness to the skin of the sanitary napkin, diaper and cloth diaper form a subenvironment that is near to be enclosed.

In the enclosed subenvironment formed by wearing sanitary napkins, diapers and cloth diapers, the increased humidity due to the absorption of body fluids, such as blood, urine and sweat, and the increased body temperature because of the upper body surface relative to the enclosed environment give rise to stuffiness and discomfort. Furthermore, personal hygiene products are not designed aseptically and all of the ambient environment, the body surface and the body fluids are likely to contain bacteria, molds and fungus. The proteins, carbohydrates and salinity of the body fluids may be used as the nutrition source of microorganisms, causing the reproduction of molds and fungus in such a high-temperature, high-humidity and high-nutrition environment. Failure to change them in time may result in infection. Therefore, a concern for the public is how to safely and conveniently provide oxygen in the semi-enclosed subenvironment of personal hygiene products, such as sanitary napkins, diapers and cloth diapers, and the like.

In prior art, peroxides are used as the solid oxidizer to produce transportable oxygen. A Japanese patent (JPA 2004536010) discloses a chemical oxygen generator wherein alkaline-earth metals ($LiClO_4$, $LiClO_3$, $NaClO_4$, $NaClO_3$, $KClO_4$ and $KClO_3$) peroxides ($Na_2O_2$ and $K_2O_2$) and superoxides ($KO_2$ and $NaO_2$) are used to produce oxygen; A Taiwan patent (application number: 083206076) discloses a mask with oxygen regenerating tank wherein sodium peroxide is used to produce oxygen. Although the above two technologies may provide oxygen, they will irritate and harm the health of human body because of too strong alkalinity if being applied to personal hygiene products contacting the body skin, such as sanitary napkins, diapers and cloth diapers.

Healthy skin is weak acidic and would be strongly irritated and even corroded if contacting hygienic products with strong alkalinity. An American patent (publication number: US20150182655) relates to a binary odor control system for absorbent articles, using calcium peroxide matched with citric acid to deodorize diapers wherein sound effect of odor control is obtained when the pulp with 0.9% citric acid and 3% Ixper 75 C (containing 75% calcium peroxide) is used, but it does not solve the problem of producing oxygen and maintaining skin-friendly pH.

Therefore, how to provide oxygen and maintain skin-friendly pH, such as being neutral, weak acidic, or slightly alkaline in personal hygiene products such as sanitary napkins, diapers, cloth diapers, pasties, insoles, disposable underwear and oxygen providing paster units, is an important subject that the present invention seeks to solve herein.

SUMMARY OF THE INVENTION

In view of the problems of stuffiness and bacteria breeding when using the sanitary napkins and diapers on the market and the harm to the skin due to the strong alkalinity if solid oxidizer is added, the present invention, after a long-time design and research by the inventor, provides a skin-friendly and oxygen providing structure which may be disposed in personal hygiene products and release oxygen after absorbing liquids with the pH remaining skin-friendly neutral, weak acidic and slightly alkaline, thereby increasing the oxygen content in the subenvironment to reach the effect of inhibiting the anaerobic bacteria with a skin-friendly pH doing no harm to the skin.

The object of the present invention is to provide a skin-friendly absorbent structure comprising an absorbing layer and skin-friendly oxygen-providing units, the skin-friendly oxygen-providing unit being evenly dispersed in partial or entire scope of the absorbing layer wherein the skin-friendly and oxygen-providing unit comprises oxygen providing units, the oxygen providing unit comprises metal peroxides, the pH regulating unit comprises solid acids, and pH regulating units and the pH of the skin-friendly absorbent structure is between 4 and 7 after absorbing liquids.

To realize the above object of the present invention, the oxygen providing unit may be further added with catalase.

To realize the above object of the present invention, the metal peroxides are selected from the group consisting of magnesium peroxide, calcium peroxide, sodium peroxide and potassium peroxide.

To realize the above object of the present invention, the solid acids are selected from the group consisting of solid citric acid, solid lactic acid, solid calcium lactate, solid oxalic acid, solid hydrochloric acid, solid phytic acid and solid silicic acid.

To realize the above object of the present invention, the skin-friendly absorbent structure may be disposed in personal hygiene products wherein the personal hygiene products comprise woundplasts, wound dressings, masks, hoods, sanitary napkins, tampons, childbed mattresses, diapers, cloth diapers, pasties, insoles, disposable underwear and oxygen providing paster units.

To realize the above object of the present invention, the preferred proportion of the oxygen providing unit to the pH regulating unit is 1:1~3.

To realize the above object of the present invention, the preferred proportion of the oxygen providing unit to the pH regulating unit is 1:1.5~2.

To realize the above object of the present invention, the catalase content in the oxygen providing unit is preferred to be 0.1 to 5%.

To realize the above object of the present invention, the catalase content in the oxygen providing unit is preferred to be 0.5 to 2%.

To realize the above object of the present invention, the pH of the skin-friendly absorbent structure is preferred to be 4 to 7 after absorbing liquids.

To realize the above object of the present invention, the pH of the skin-friendly absorbent structure is preferred to be 4 to 5.5. after absorbing liquids.

SYMBOL DESCRIPTION OF MAIN ELEMENT

| | |
|---|---|
| 1 | Skin-friendly absorbent structure |
| 101 | Absorbing layer |
| 102 | Skin-friendly oxygen-providing unit |
| 2 | Sanitary napkin |
| 3 | Woundplast |
| 4 | Diaper |

DETAILED DESCRIPTION OF THE PREFERRED EMBODIMENT

The present invention is exemplarily illustrated by but not limited to following embodiments.

Figure 1:
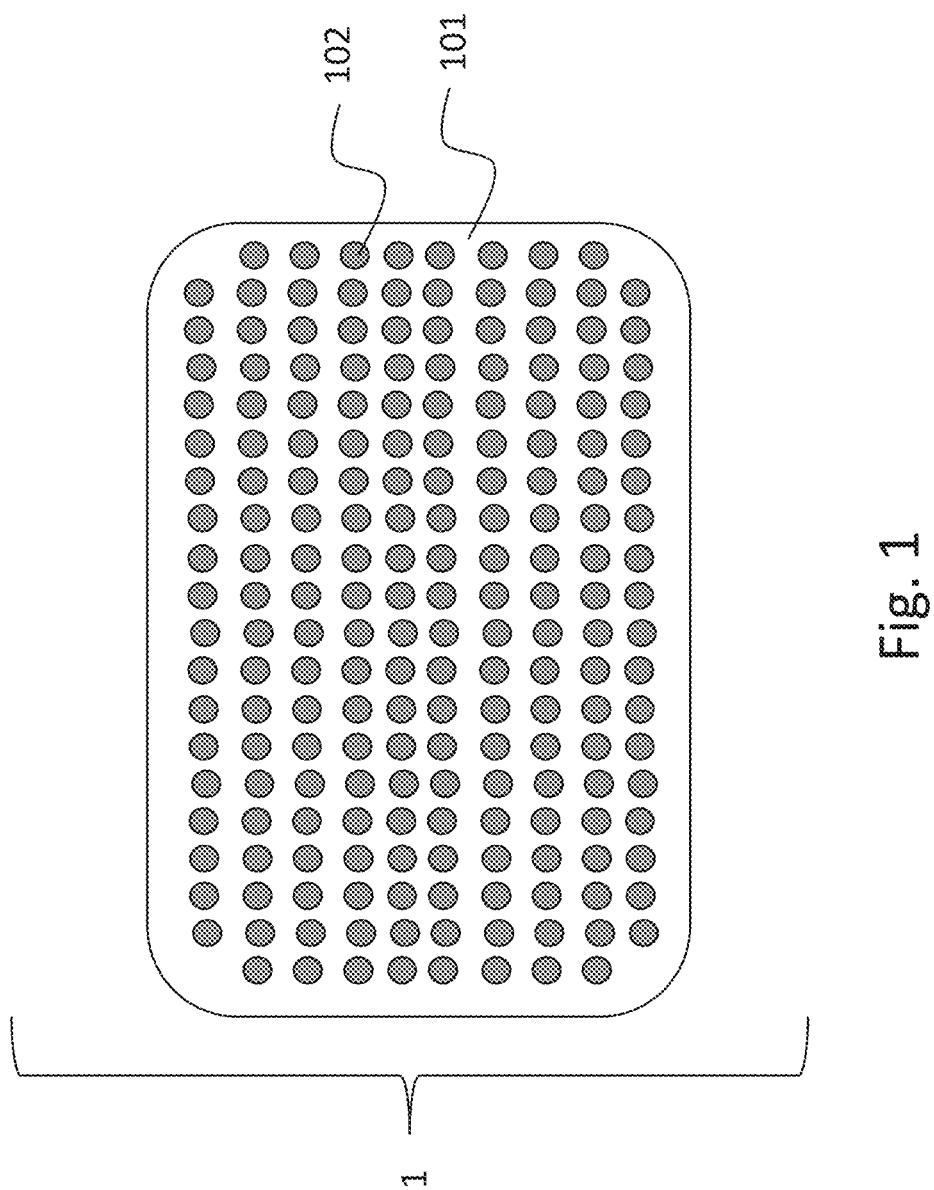
FIG. 1 is the schematic diagram of the present invention, illustrating a skin-friendly absorbent structure providing oxygen comprising skin-friendly oxygen-providing units and a absorbing layer wherein the skin-friendly and oxygen providing units are evenly dispersed in the entire scope of the absorbing layer.
Figure 2:
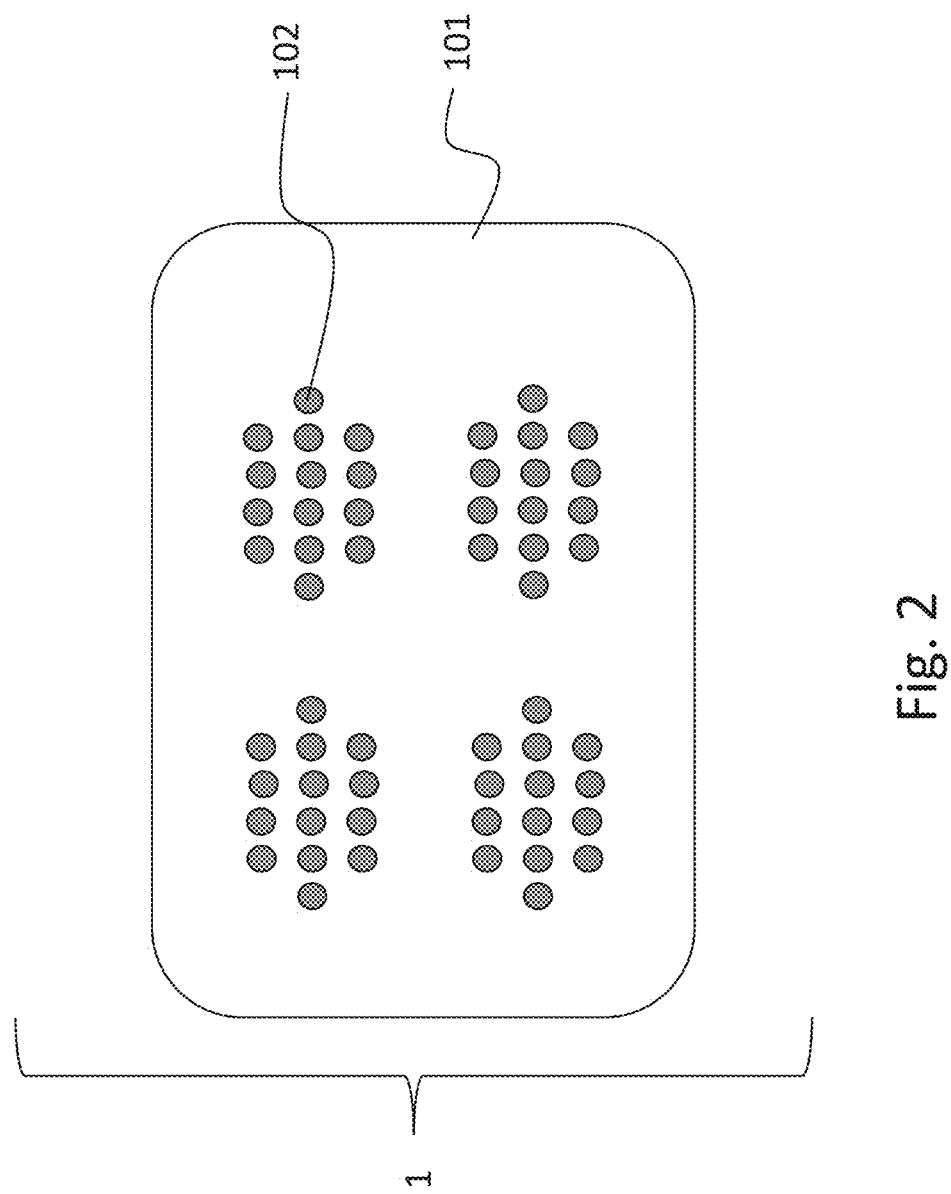
FIG. 2 is the schematic diagram of the present invention, illustrating a skin-friendly absorbent structure providing oxygen comprising skin-friendly and oxygen providing units and a absorbing layer wherein the skin-friendly and oxygen providing units are evenly dispersed in the partial scope of the absorbing layer.
Figure 3:
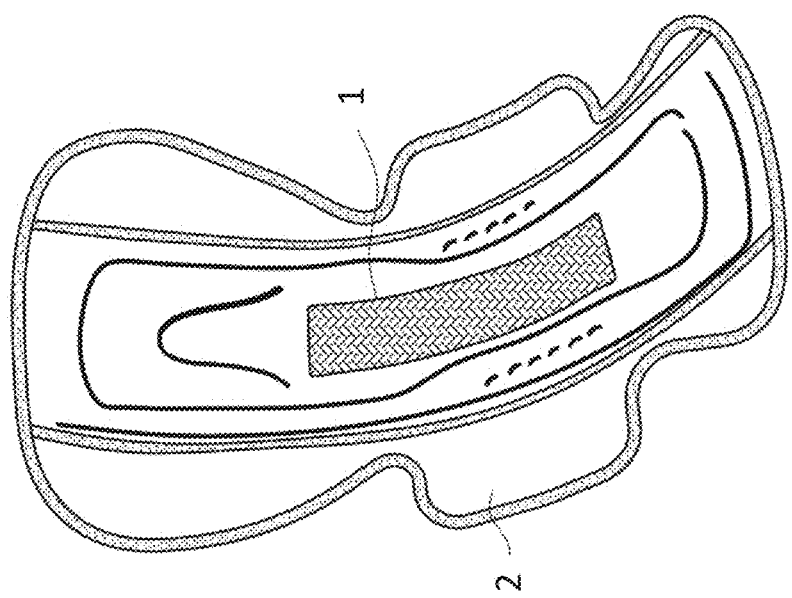
FIG. 3 is the schematic diagram of the use of one preferred embodiment of the present invention for illustrating the skin-friendly absorbent structure providing oxygen disposed in a sanitary napkin.
Figure 4:
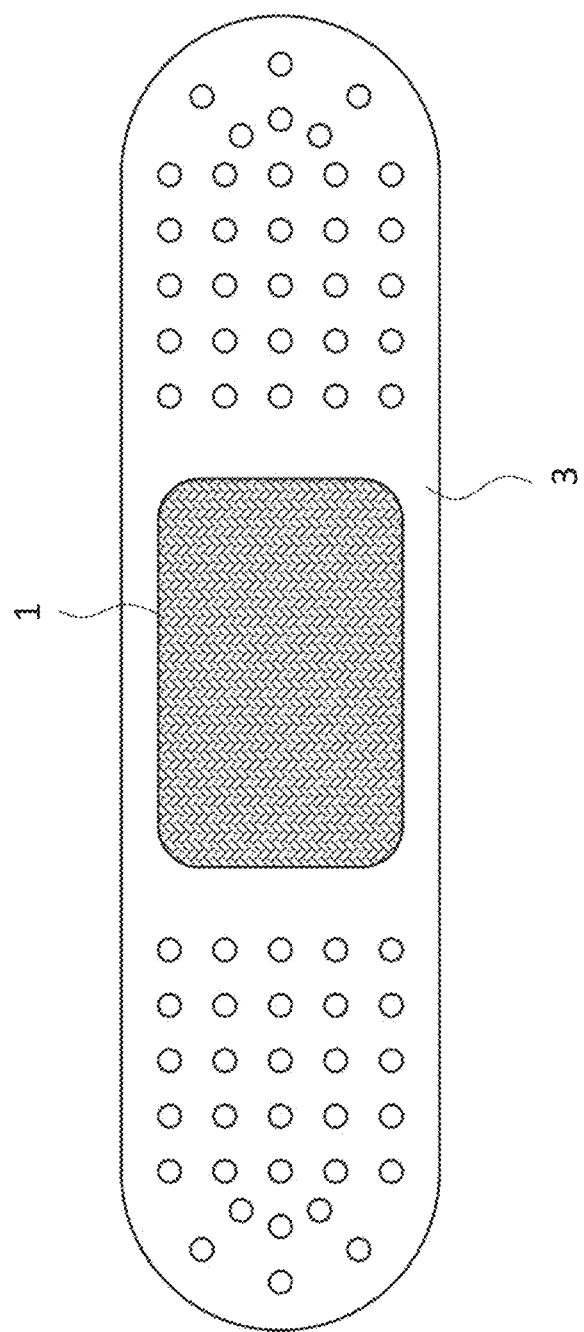
FIG. 4 is the schematic diagram of the use of one preferred embodiment of the present invention for illustrating the skin-friendly absorbent structure providing oxygen disposed in a woundplast.
Figure 5:
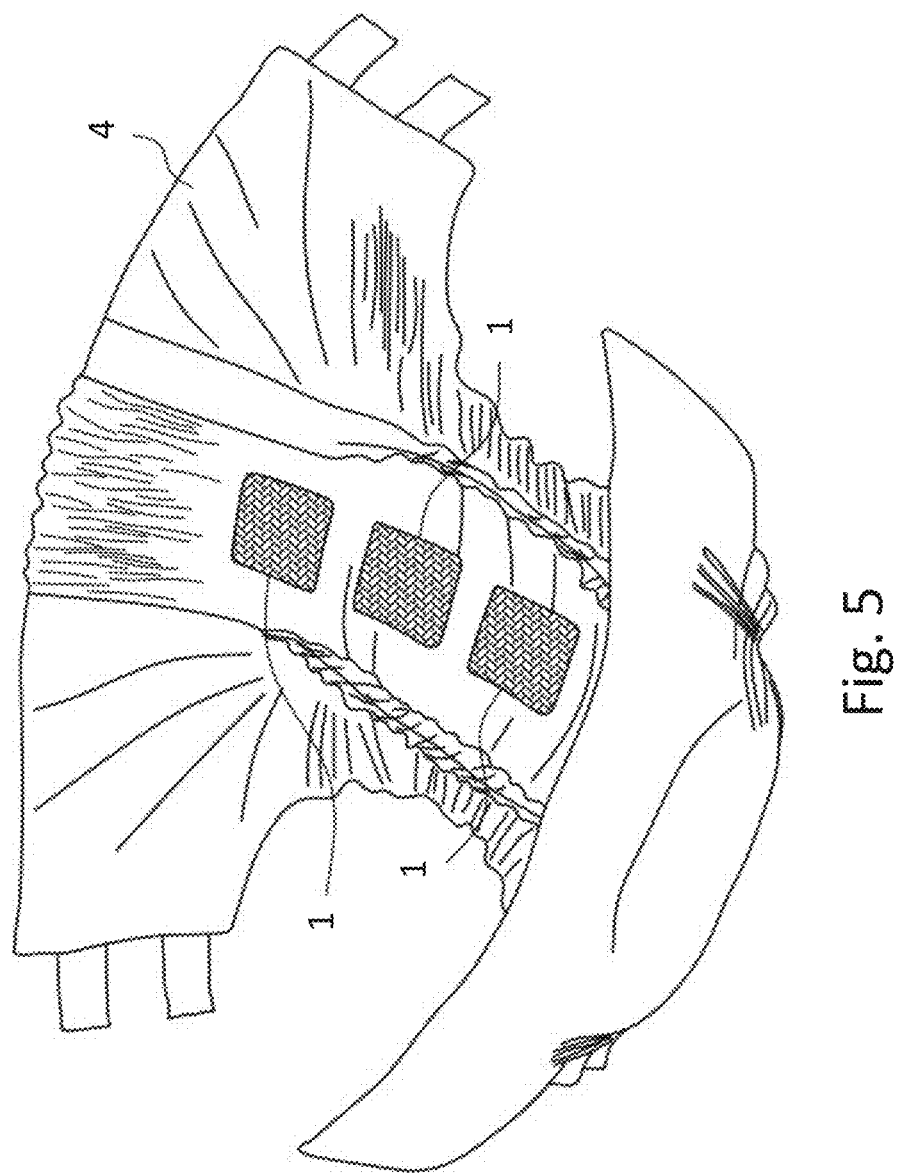
FIG. 5 is the schematic diagram of the use of one preferred embodiment of the present invention for illustrating the skin-friendly absorbent structure providing oxygen disposed in a diaper wherein the diaper may contain one or more skin-friendly absorbent structures for providing oxygen.

The present invention is a skin-friendly absorbent structure providing oxygen which may release oxygen after absorbing moisture with the pH remaining skin-friendly neutral, weak acidic and slightly alkaline, and the skin-friendly absorbent structure providing oxygen (1) comprises a absorbing layer (101) and skin-friendly and oxygen providing units (102) wherein the skin-friendly and oxygen providing units are evenly dispersed in the entire (FIG. 1) or partial (FIG. 2) scope of the absorbing layer; With reference to FIGS. 3, 4 and 5, the illustrated skin-friendly absorbent structure providing oxygen (1) may be disposed in personal hygienic products, such as a sanitary napkin (3), a woundplast (4) and a diaper (5), to increase the oxygen content in the subenvironment because the increased oxygen also inhibits the growth of the anaerobic bacteria.

Embodiment One

The Diaper Containing Magnesium Peroxide and Lactic Acid $2MgO_2+2H_2O \rightarrow 2Mg(OH)_2+O_2$   $2CH_3CH(OH)COOH+Mg(OH)_2 \rightarrow (C_3H_5O_3)_2Mg+2H_2O$ The diaper contains magnesium peroxide and lactic acid. When not in use, the diaper is dried wherein the magnesium peroxide and lactic acid are solid having no effect on the pH; When in use, the magnesium peroxide of the diaper will produce magnesium hydroxide and oxygen after absorbing the moisture of the urine, reducing the moisture but increasing the oxygen in the subenvironment of the diaper so that the growth of the anaerobic bacteria is inhibited; And when encountering the magnesium hydroxide, the lactic acid will release hydrogen ions ($H^+$) which will neutrally react with the hydroxyl ions ($OH^-$) of the magnesium hydroxide, transforming into magnesium lactate and water along with a little produced oxygen wherein the magnesium lactate is weak acidic, doing no harm to the skin.

Embodiment Two

The Sanitary Napkin Containing Calcium Peroxide and Citric Acid

The sanitary napkin contains 1 g calcium peroxide and 2 g citric acid. When not in use, the sanitary napkin is dried wherein the calcium peroxide and the citric acid are solid which have no effect on the pH; when in use, the calcium peroxide of the sanitary napkin absorbs the moisture of the blood, producing calcium hydroxide and oxygen. When encountering the calcium hydroxide, the citric acid will release hydrogen ions ($H^+$) which will neutrally react with the hydroxyl ions ($OH^-$) of the calcium hydroxide. After adding 100 ml water to 1 g calcium peroxide and 2 g citric acid of the sanitary napkin and stirring them sufficiently for 5 minutes, the pH is 4.82, being weak acidic and a little oxygen is produced; Comparing with the prior art (US20150182655) containing the pulp with 0.9% citric acid and 3% Ixper 75 C (containing 75% calcium peroxide), 100 ml water is added to 2.25 g calcium peroxide and 0.95 g citric acid in the same proportion and after stirring them sufficiently for 5 minutes, the pH is up to 12.10 and a lot of hydrogen peroxide instead of oxygen is produced with great harm to the skin.

As the oxygen producing process is slow after adding water to 1 g calcium peroxide and 2 g citric acid, catalase is further added wherein the calcium peroxide will produce calcium hydroxide and hydrogen peroxide after absorbing the moisture and when encountering the catalase (short for CAT), the hydrogen peroxide will rapidly produce oxygen while the citric acid, upon encountering the calcium hydroxide, will release hydrogen ions ($H^+$) which will neutrally react with the hydroxyl ions ($OH^-$) of the calcium hydroxide, the reaction formula being as follows:

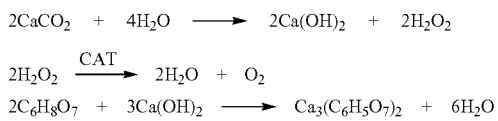

After adding 100 ml water to 1 g calcium peroxide, 2 g citric acid and catalase and stirring them sufficiently for 5 minutes, the oxygen is rapidly produced, inhibiting the growth of the anaerobic bacteria, and the pH of the liquid is 4.82 which is weak acidic, having no irritating effect on the skin and giving a comfortable feeling.

Embodiment Three

A Woundplast Able to Produce Oxygen with a Skin-Friendly pH.

The absorbing layer of the woundplast contains fibers sprayed with solid lactic acid, fibers sprayed with solid oxalic acid and fibers sprayed with solid sodium peroxide. When not in use, the woundplast is dried wherein the lactic acid, the oxalic acid and the sodium peroxide are solid, having no effect on the pH.

When in use, the woundplast absorbs the moisture of the blood from the wound, producing sodium lactate, sodium oxalate and oxygen. At the moment, in the subenvironment of the woundplast, the moisture is reduced and the oxygen is increased, inhibiting the growth of the anaerobic bacteria, and the proportion of the lactic acid, the oxalic acid and the sodium peroxide may be adjusted to make the pH thereof is between 4 and 9, doing no harm to the skin, after encountering water.

Embodiment Four

A Sanitary Napkin Able to Steadily Produce Oxygen with a Skin-Friendly pH

The sanitary napkin contains calcium peroxide, oxalic acid, citric acid and catalase in the proportion of 5:2.3:6:0.05. When not in use, the sanitary napkin is dried wherein the calcium peroxide, the oxalic acid, the citric acid and the catalase are solid, having no effect on the pH; When in use, the calcium peroxide absorbs the moisture of the blood, producing calcium hydroxide and hydrogen peroxide. When encountering the catalase, the hydrogen peroxide will rapidly produce oxygen while the oxalic acid and the citric acid, upon encountering the calcium hydroxide, will release hydrogen ions ($H^+$) which will neutrally react with the hydroxyl ions ($OH^-$) of the calcium hydroxide. After adding 100 ml water to the calcium peroxide, the oxalic acid, the citric acid and the catalase in the proportion of 5:2.3:6:0.05 and stirring them sufficiently for 5 minutes, the oxygen is rapidly produced, inhibiting the growth of the anaerobic bacteria, and the pH of the liquid is 4.82 which is weak acidic, having no irritating effect on the skin and giving a comfortable feeling.

Different metal peroxides may be used for matching with different solid acids wherein the metal peroxides comprise magnesium peroxide, calcium peroxide, sodium peroxide and potassium peroxide and the solid acids comprise citric acid, lactic acid, calcium lactate, oxalic acid, hydrochloric acid, phytic acid and silicic acid. The metal peroxides and the solid acids are matched in different proportions and after adding water, if the pH is 4 to 9, it has no irritating effect on the skin and if the pH is 4 to 5.5, it may make the skin feel comfortable.

Embodiment Five

Oxygen Providing Paster Unit

The materials of the absorbing layer contain non-woven fabrics, gauzes and the like water absorbing materials. Solid oxides, solid acids and catalase are mixed evenly and then sprayed on the absorbing layer to form the oxygen providing paster unit. The oxygen providing paster unit may be attached to the parts of the body that needs to be provided with oxygen, such as the wound.

In addition to direct use of the oxygen providing paster unit, the wound may also be dressed firstly with a woundplast and then the oxygen providing paster unit is used to cover the woundplast. At the moment, the moisture produced by the wound will be released to the oxygen providing paster unit through the woundplast and the oxygen produced by the oxygen providing paster unit reaches the wound through the woundplast At this moment, in the subenvironment of the oxygen providing paster unit outside of the wound, oxygen is greatly increased and the skin-friendly pH is maintained.

The above-mentioned detailed description aims to specifically illustrate the practicable embodiments of the present invention, but the embodiments are not for limiting the patent scope of the present invention and all equivalent embodiments or modifications made without departing from the spirit of the present invention shall be contained within the patent scope of the present invention.

The plentiful effects above-mentioned meet the lawful patent requirement for novelty and inventiveness. The inventor files an application according to law and earnestly urge honorable Office to approve the patent application of the present invention as an encouragement thereof.

What is claimed is:

1. A skin-friendly absorbent structure providing oxygen, comprising an absorbing layer and skin-friendly oxygen-providing units, the skin-friendly oxygen-providing units being evenly dispersed and spaced apart from one another in a regular pattern over the absorbing layer, wherein the skin-friendly oxygen-providing units each comprise an oxygen-providing unit and a pH regulating unit; wherein the oxygen-providing unit comprises solid metal peroxides selected from the group consisting of magnesium peroxide, calcium peroxide, sodium peroxide and potassium peroxide; wherein the pH regulating unit comprises solid acids selected from the group consisting of solid oxalic acid, solid hydrochloric acid, solid phytic acid and solid silicic acid, and the pH of the skin-friendly absorbent structure is between 4 and 9 after absorbing liquids.

2. The skin-friendly absorbent structure according to claim 1, wherein the oxygen-providing unit may be further added with catalase.

3. The skin-friendly absorbent structure according to claim 2, wherein the catalase content in the oxygen-providing unit is 0.1~5%.

4. The skin-friendly absorbent structure according to claim 2, wherein the catalase content in the oxygen-providing unit is 0.5~2%.

5. The skin-friendly absorbent structure according to claim 1, wherein the skin-friendly absorbent structure is disposed in a personal hygiene product, wherein the personal hygiene product comprises woundplasts, wound dressings, masks, hoods, sanitary napkins, tampons, childbed mattresses, diapers, cloth diapers, pasties, insoles, disposable underwear or oxygen providing paster units.

6. The skin-friendly absorbent structure according to claim 1, wherein the proportion of the oxygen-providing unit to the pH regulating unit is 1:1~3.

7. The skin-friendly absorbent structure according to claim 1, wherein the proportion of the oxygen-providing unit to the pH regulating unit is 1:1.5~2.

8. The skin-friendly absorbent structure according to claim 1, wherein the pH of the skin-friendly absorbent structure is 4 to 7 after absorbing liquids.

9. The skin-friendly absorbent structure according to claim 1, wherein the pH of the skin-friendly absorbent structure is 4 to 5.5 after absorbing liquids.

* * * * *